US012606820B2

(12) United States Patent

Huang et al.

(10) Patent No.: US 12,606,820 B2

(45) Date of Patent: Apr. 21, 2026

(54) GENOME-WIDE INSULATOR SCREENING SYSTEM AND USE

(71) Applicant: Agricultural Genomics Institute at Shenzhen, Chinese Academy of Agricultural Sciences, Guangdong (CN)

(72) Inventors: Lei Huang, Guangdong (CN); Yuwen Liu, Guangdong (CN); Xiusheng Zhu, Guangdong (CN)

(73) Assignee: Agricultural Genomics Institute at Shenzhen, Chinese Academy of Agricultural Sciences, Shenzhen (CN)

( * ) Notice: Subject to any disclaimer, the term of this patent is extended or adjusted under 35 U.S.C. 154(b) by 0 days.

(21) Appl. No.: 19/021,326

(22) Filed: Jan. 15, 2025

(65) Prior Publication Data

US 2026/0085307 A1 Mar. 26, 2026

(30) Foreign Application Priority Data

Sep. 24, 2024 (CN) .......................... 202411329018.6

(51) Int. Cl.
*C12N 15/113* (2010.01)
*C12N 15/10* (2006.01)
(Continued)

(52) U.S. Cl.
CPC ......... *C12N 15/1082* (2013.01); *C12N 15/66* (2013.01); *C12Q 1/6806* (2013.01); (Continued)

(58) Field of Classification Search
None
See application file for complete search history.

(56) References Cited

FOREIGN PATENT DOCUMENTS

| CN | 110885845 A | 3/2020 |
| CN | 112538493 A | 3/2021 |

(Continued)

OTHER PUBLICATIONS

Doni Jayavelu, N., Jajodia, A., Mishra, A. et al. Candidate silencer elements for the human and mouse genomes. Nat Commun 11, 1061 (2020). https://doi.org/10.1038/s41467-020-14853-5.

(Continued)

*Primary Examiner* — Heather Calamita
*Assistant Examiner* — Elizabeth Rose LaFave
(74) *Attorney, Agent, or Firm* — Rondaus PLLC; George Liu

(57) ABSTRACT

The present disclosure discloses a genome-wide insulator screening system. The system comprises an MAI-seq-experiment vector and an MAI-seq-control vector; core gene elements in the MAI-seq-experiment vector are arranged in following order: a weak promoter, a marker target gene, an insertion site for a sequence to be screened, an enhancer and a poly A site; and core gene elements in the MAI-seq-control vector are arranged in following order: a weak promoter, a marker target gene, an enhancer, an insertion site for the sequence to be screened and a poly A site. This genome-wide insulator screening system, primarily composed of these two vectors, exhibits high sensitivity and can be applied to the screening of genomic insulators in any species. Furthermore, it effectively eliminates the influence of silencers, ensuring high screening accuracy. This system provides important technical support for constructing insulator maps and understanding the characteristics and mechanisms of action of insulators.

4 Claims, 3 Drawing Sheets

Specification includes a Sequence Listing.

(51) Int. Cl.

| | |
|---|---|
| *C12N 15/66* | (2006.01) |
| *C12Q 1/6806* | (2018.01) |
| *C12Q 1/6809* | (2018.01) |
| *C12Q 1/6855* | (2018.01) |
| *C12Q 1/686* | (2018.01) |
| *C12Q 1/6869* | (2018.01) |
| *C12N 15/00* | (2006.01) |

(52) U.S. Cl.
CPC ......... *C12Q 1/6809* (2013.01); *C12Q 1/6855* (2013.01); *C12Q 1/686* (2013.01); *C12Q 1/6869* (2013.01); *C12N 2830/50* (2013.01)

(56) References Cited

FOREIGN PATENT DOCUMENTS

| | | | | | |
|---|---|---|---|---|---|
| CN | 116286991 | A | 6/2023 | | |
| KR | 1020150039104 | A | 4/2015 | | |
| WO | WO-2021155040 | A1 * | 8/2021 | ............ | B01L 3/5025 |
| WO | WO-2022235764 | A1 * | 11/2022 | ......... | G01N 21/6452 |

OTHER PUBLICATIONS

Chan, YC., Kienle, E., Oti, M. et al. An unbiased AAV-STARR-seq screen revealing the enhancer activity map of genomic regions in the mouse brain in vivo. Sci Rep 13, 6745 (2023). https://doi.org/10.1038/s41598-023-33448-w.

* cited by examiner

MAI-seq-control(miniP-SV40-insulator)

GENOME-WIDE INSULATOR SCREENING SYSTEM AND USE

SEQUENCE LISTING

This application contains a sequence listing, the copy of which is named SEQ GENOME-WIDE INSULATOR SCREENING SYSTEM AND USE THEREOF .xml, created on Jan. 6, 2025, and has a size of 19,797 bytes.

TECHNICAL FIELD

The present disclosure relates to the field of genetic engineering, particularly to a genome-wide insulator screening system and use thereof.

BACKGROUND

Cis-acting elements are non-coding DNA regions that regulate gene expression by binding to transcription factors, thereby controlling the precise initiation of gene transcription and transcriptional efficiency. These cis-regulatory elements mainly include promoters, enhancers, silencers, and the relatively less-studied insulators. Insulators were initially discovered in *Drosophila* cells, and their molecular mechanisms have since been elucidated. When located between a gene and an enhancer, insulators can prevent the enhancer from exerting its effect on the target gene. Additionally, insulators can block the repressive effects of heterochromatin near active genes on those active genes. Insulators play a crucial role in the structure and function of the mammalian genome, but little is known about how insulators exert their functional specificity, primarily due to the lack of effective methods for insulator identification.

SUMMARY

The objective of the present disclosure is to provide a genome-wide insulator screening system and use thereof, which can be efficiently used for screening genomic insulators in any species. The construction method and use of this screening system provide important support for constructing insulator maps and understanding the characteristics and mechanisms of action of insulators.

In the first aspect, the present disclosure provides a genome-wide insulator screening system. The system comprises an MAI-seq-experiment vector and an MAI-seq-control vector; core gene elements in the MAI-seq-experiment vector are arranged in following order: a weak promoter, a marker target gene, an insertion site for a sequence to be screened, an enhancer and a poly A site; and core gene elements in the MAI-seq-control vector are arranged in following order: a weak promoter, a marker target gene, an enhancer, an insertion site for the sequence to be screened and a poly A site. Thus, this genome-wide insulator screening system, primarily composed of these two vectors, exhibits high sensitivity and can be applied to the screening of genomic insulators in any species. Furthermore, it effectively eliminates the influence of silencers, ensuring high screening accuracy. This system provides important technical support for constructing insulator maps and understanding the characteristics and mechanisms of action of insulators.

In some embodiments, the insertion site for the sequence to be screened contains homologous arm sequences that are arranged to undergo homologous recombination, and after two ends of a DNA sequence to be screened are added to the homologous arm sequences, homologous recombination occurs with either the MAI-seq-experiment vector or the MAI-seq-control vector.

In some embodiments, a nucleotide sequence of the MAI-seq-experiment vector is as shown in SEQ ID NO:1, and a nucleotide sequence of the MAI-seq-control vector is as shown in SEQ ID NO:2.

In the second aspect, the present disclosure provides a use of the aforementioned genome-wide insulator screening system in screening for genomic insulators. This use involves fragmenting the gene sequence to be tested, adding Illumina® sequencing adapters, and performing PCR amplification using primers containing homology arms that can undergo homologous recombination with the screening system vectors. This process adds homology arm sequences to both ends of the DNA fragments of the gene sequence to be tested, enabling them to undergo homologous recombination and insertion at specified locations in the screening system vectors. Leveraging the position-dependent manner in which insulators function, this use not only facilitates the screening of insulators but also effectively eliminates the influence of silencers. The system and use method are simple, efficient, highly sensitive, and applicable to any species.

In some embodiments, the use comprises following steps:

S1: fragmenting a gene sequence to be tested, ligating the fragmented gene segments with Illumina® sequencing adapters, and performing PCR amplification using primers as shown in SEQ ID NO:5 and SEQ ID NO:6;

S2: homologously recombining PCR products from S1 into the MAI-seq-experiment vector and the MAI-seq-control vector to construct homologous recombination plasmids;

S3: transforming the homologous recombination plasmids constructed in S2 and extracting the plasmids to obtain an Input library for the MAI-seq-experiment vector and an Input library for the MAI-seq-control vector, respectively, and performing high-throughput sequencing on the Input libraries;

S4: transfecting cells with the Input libraries of the MAI-seq-experiment vector and the MAI-seq-control vector constructed in S3, collecting the cells, performing reverse transcription amplification, collecting amplified products to prepare an Output library for the MAI-seq-experiment vector and an Output library for the MAI-seq-control vector, respectively, and performing high-throughput sequencing on the Output libraries;

S5: by comparing a sequencing data of the Input and Output libraries of the MAI-seq-experiment vector, screening out sequences with reduced transcription abundance in the Output library compared to the Input library;

S6: by comparing a sequencing data of the Input and Output libraries of the MAI-seq-control vector, screening out sequences with reduced transcription abundance in the Output library compared to the Input library; and S7: removing from the sequences screened out in S5 those that are duplicated in the sequences screened out in S6, with the remaining sequences being the screened insulator sequences.

In the third aspect, the present disclosure provides a use of the aforementioned genome-wide insulator screening system in validating genomic insulators. Thereby, this use merely requires amplifying the sequence to be validated by PCR using primers containing homology arms that can undergo homologous recombination with the MAI-seq-experiment vector in the genome-wide insulator screening system. The amplified sequence to be validated, containing homology arms, is then homologously recombined with the MAI-seq-experiment vector and inserted into the specified location. By detecting changes in the expression level of the marker target gene, it is possible to validate whether the sequence is an insulator sequence.

In some embodiments, the use comprises following steps:

S1: inserting the sequence to be validated into the MAI-seq-experiment vector to construct a validation plasmid;

S2: using the MAI-seq-experiment vector without any sequence inserted as a blank control plasmid; and S3: transfecting cells with the blank control plasmid and the validation plasmid separately, collecting cells 48 hours post-transfection to extract RNA, and utilizing qPCR to detect changes in the expression level of the marker target gene. If the expression level of the marker target gene in the validation plasmid group decreases, it proves that the sequence to be validated is an insulator; otherwise, it is not.

In the fourth aspect, the present disclosure provides a use of the aforementioned genome-wide insulator screening system in a preparation of a kit or a product for screening or validating genomic insulators.

In the fifth aspect, the present disclosure provides an insulator validation vector. The insulator validation vector is the MAI-seq-experiment vector with its nucleotide sequence shown in SEQ ID NO:1. Thereby, using this MAI-seq-experiment vector, one only needs to insert the sequence to be validated into a designated position of the vector via homologous recombination, and then by comparing the abundance of the marker target gene expression, it is possible to preliminarily determine whether the sequence to be validated is an insulator in a simple, rapid, efficient, and convenient manner.

In the sixth aspect, the present disclosure provides a use of the aforementioned insulator validation vector in the screening and validation of insulators.

The beneficial effects of the present disclosure are as follows:

1. The genome-wide insulator screening system disclosed in the present disclosure primarily consists of two vectors, exhibiting high sensitivity and applicability for screening genomic insulators in any species. Moreover, it effectively eliminates the influence of silencers, ensuring high screening accuracy. This system provides crucial technical support for constructing insulator maps and understanding the characteristics and mechanisms of action of insulators.

2. The present disclosure discloses a use of the genome-wide insulator screening system in screening for genomic insulators and a use method. This method involves fragmenting the gene sequence to be tested and adding Illumina® sequencing adapters. Subsequently, PCR amplification is performed using primers containing homology arms that can recombine homologously with the vectors in the genome-wide insulator screening system. This results in the addition of homology arm sequences to both ends of the DNA fragments of the gene sequence to be tested. These homology arms enable the DNA fragments of the gene sequence to be tested to recombine homologously with the vector and be inserted into a specified position. By leveraging the position-dependent functionality of insulators, the screening of insulators is achieved, effectively eliminating the influence of silencers. This system and use method are simple, efficient, highly sensitive, and applicable to any species.

3. The present disclosure also discloses a use of the genome-wide insulator screening system in validating genomic insulators and a use method. This method merely requires amplifying the sequence to be validated by PCR using primers containing homology arms that can undergo homologous recombination with the MAI-seq-experiment vector in the genome-wide insulator screening system. The amplified sequence to be validated, containing homology arms, is then homologously recombined with the MAI-seq-experiment vector and inserted into the specified location. By detecting changes in the expression level of the marker target gene, it is possible to validate whether the sequence is an insulator sequence.

4. Furthermore, the present disclosure discloses an insulator validation vector. Using this MAI-seq-experiment vector, one only needs to insert the sequence to be validated into a designated position of the vector via homologous recombination, and then by comparing the abundance of the marker target gene expression, it is possible to determine whether the sequence is an insulator in a simple, rapid, efficient, and convenient manner.

DETAILED DESCRIPTION OF THE EMBODIMENTS

The present disclosure is further described in detail below with reference to the accompanying drawings.

Figure 1:
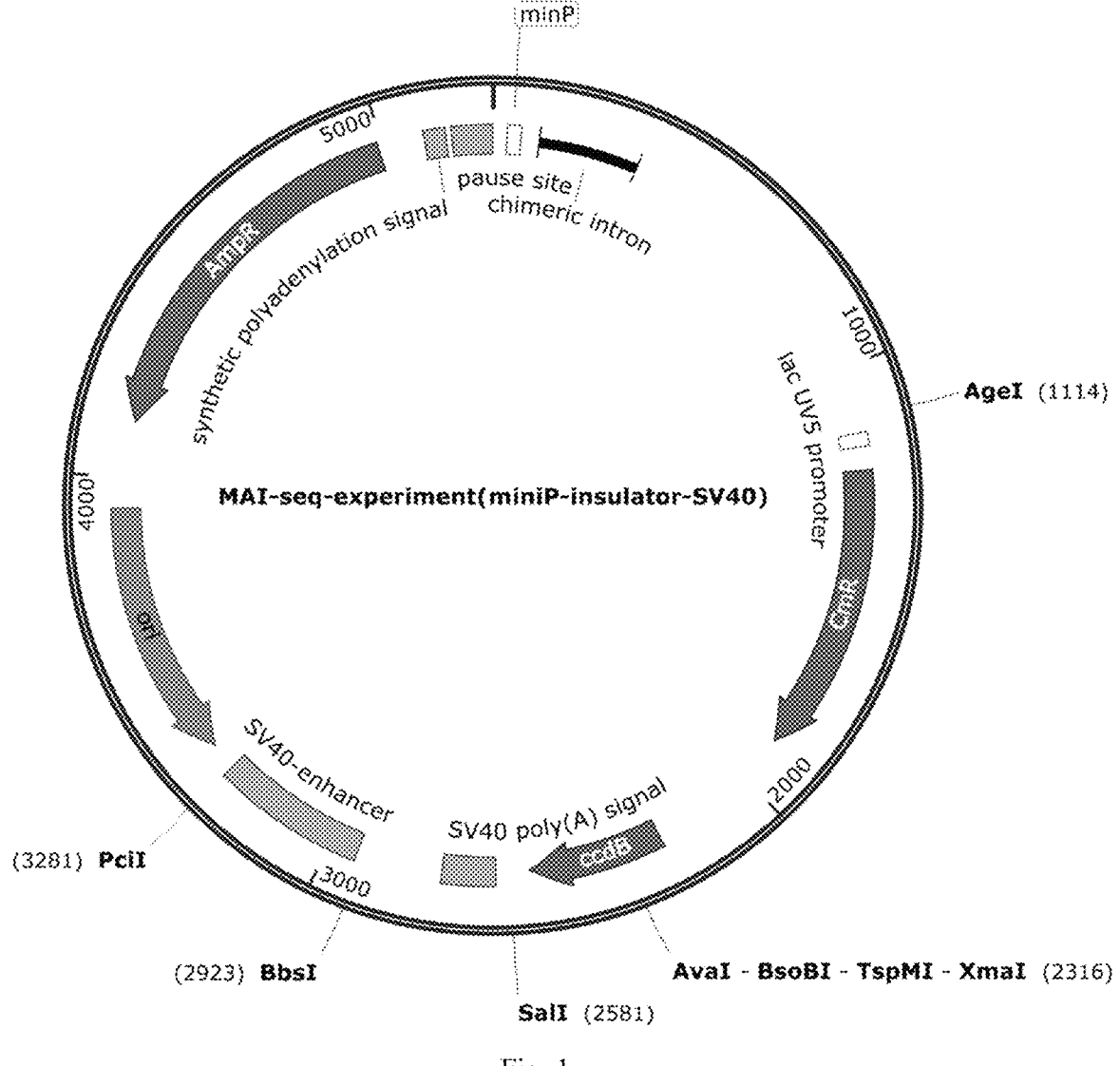
FIG. 1 shows the structural diagram of the MAI-seq-experiment vector.
Figure 2:
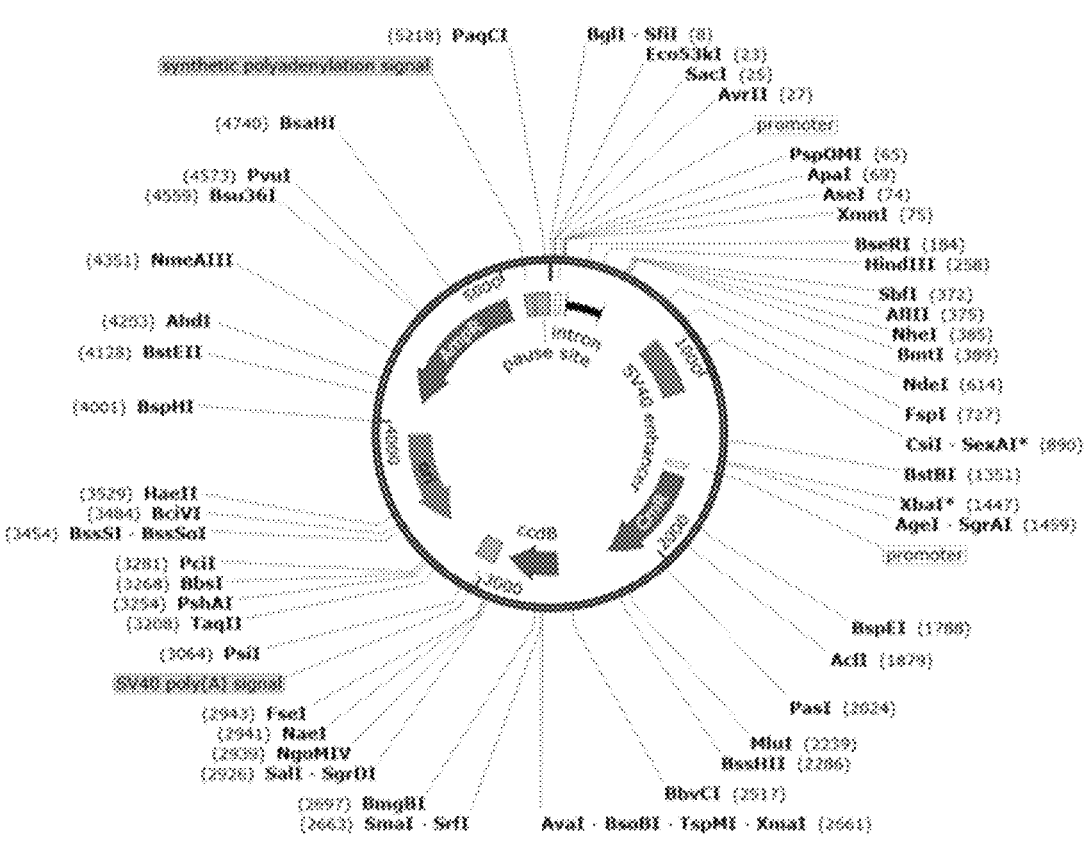
FIG. 2 shows the structural diagram of the MAI-seq-control vector.

Embodiment 1: Construction of the Genome-Wide
Insulator Screening System MAI-Seq 1. Construction Method of the Genome-Wide Insulator
Screening System MAI-Seq The genome-wide insulator screening system MAI-seq
consists of two sets of vectors (a dual-vector system). The
first vector is MAI-seq-experiment (as shown in FIG. 1),
with its nucleotide sequence provided in SEQ ID NO:1. This
vector is modified from the STARR-seq vector (addgene,
711509). Specifically, the SCP1 promoter of the STARR-seq
vector is replaced with a Mini-promoter (a weak promoter
containing an incomplete promoter sequence with a TATA-
box, which requires interaction with an enhancer for tran-
scription), and the SV40 enhancer sequence is inserted
between the restriction enzyme sites BbsI and PciI. The
second vector is MAI-seq-control (as shown in FIG. 2), with
its nucleotide sequence provided in SEQ ID NO:2. This
vector is also modified from the STARR-seq vector. Spe-
cifically, the SCP1 promoter of the STARR-seq vector is
replaced with a Mini-promoter (a weak promoter), and the
SV40 enhancer sequence is inserted at the BsaAI-PmlI site.
The difference between the MAI-seq-experiment vector and
the MAI-seq-control vector lies in the position of the SV40
enhancer, leading to distinct functions of the two.

2. Working Principle of the Genome-Wide Insulator Screen-
ing System MAI-Seq

Figure 3:
FIG. 3 shows a schematic diagram of the main gene sequence of the MAI-seq-experiment vector, where Mini Promoter represents the weak promoter Mini Promoter sequence, Green Fluorescent Protein (GFP) stands for the marker gene GFP sequence, Insulator serves as the insertion site for the sequence to be screened, SV40 Enhancer denotes the enhancer SV40 Enhancer sequence, and poly (A) signal signifies the poly A site sequence.

Insulators function in a position-dependent manner, only
blocking the activation of target gene transcription by an
enhancer when placed between the enhancer and the target
gene. If the insulator is located elsewhere, it cannot prevent
the enhancer from activating the target gene transcription.
Therefore, the sequence to be screened is inserted between
a "weak promoter, Mini Promoter" and an "enhancer, SV40
Enhancer." In this way, sequences with insulator activity can
block or attenuate the transcription of the target gene. The
strength of each insulator can be reflected by the relative
transcription abundance of the target gene within the cells.
As shown in FIG. 3: When the sequence to be screened or
identified (located at the "Insulator" position in FIG. 3) is an
insulator, it will prevent the interaction between the
"enhancer, SV40 Enhancer" and the "weak promoter, Mini
Promoter," thereby reducing the expression level of the
marker gene GFP (the target gene). The transcription abun-
dance and expression of the marker gene GFP will decrease.
The strength of the insulator can be identified based on the
degree of reduction in transcription abundance. Conversely,
when the sequence to be screened or identified is not an
insulator, the interaction between the "enhancer, SV40
Enhancer" and the "weak promoter, Mini Promoter" can
activate the expression of the marker gene GFP, resulting in
higher transcription abundance and expression levels of the
marker gene GFP.

The reason for using the weak promoter, Mini Promoter,
is that it can eliminate the influence of silencers to some
extent. If a non-weak promoter (such as a strong promoter
or a normal promoter) is used, when the sequence to be
screened is a silencer, it may also lead to a decrease in the
transcription abundance of the marker gene within the cells.
In this case, some silencers may be mistakenly identified as
insulators, resulting in false positives. Therefore, the two
vectors of this system must use the interaction between a
weak promoter and an enhancer to screen and identify
insulators.

In the genome-wide insulator screening system MAI-seq,
the core part of the MAI-seq experiment is shown in FIG. 3.
Briefly, the sequence to be tested is inserted into the "Insulator" position in FIG. 3 through homologous recombination
to obtain a homologous recombination plasmid. These plas-
mids are then pooled to construct an input library. Subse-
quently, the input library is transfected into cells, and cells
are collected 24 hours later to construct an output library.
For each sequence to be tested, if it possesses insulator
activity, it can block the interaction between the Mini
Promoter and the SV40 enhancer, thereby reducing the
transcription abundance of the downstream target gene
(GFP) sequence driven by the Mini Promoter. At the same
time, the sequence to be tested will also be transcribed. By
comparing the differences in transcription abundance of the
sequence to be tested between the input and output libraries,
it is possible to determine which sequences have insulator
activity (if the sequence to be tested is an insulator, its
transcription abundance in the output library will be lower
than that in the input library).

Figure 4:
FIG. 4 shows a schematic diagram of the main gene sequence of the MAI-seq-control vector, where Mini Promoter represents the weak promoter Mini Promoter sequence, GFP stands for the marker gene GFP sequence, SV40 Enhancer denotes the enhancer SV40 Enhancer sequence, Insulator serves as the insertion site for the sequence to be screened, and poly (A) signal signifies the poly A site sequence.

Although the use of a weak promoter in the MAI-seq-
experiment vector can avoid the influence of silencers on the
screening results to some extent, to completely eliminate the
impact of silencers, the system also includes the MAI-seq-
control vector, whose core part is shown in FIG. 4. This is
because insulators only exert their blocking effect when
positioned between a promoter and an enhancer, whereas
silencers can exert their blocking effect regardless of their
position. Therefore, when the sequence to be tested is
inserted into the "Insulator" position in FIG. 4, it will be
selected and identified as having silencer activity only if it
inhibits transcription. If the sequence to be tested is an
insulator, it cannot inhibit transcription because it is not
located between the promoter and the enhancer. Thus, the
MAI-seq-control vector can be used to screen for silencer
sequences.

By comparing the sequences screened using the MAI-
seq-experiment and MAI-seq-control vectors, first list the
sequences screened by the MAI-seq-experiment vector, and
then list the sequences screened by the MAI-seq-control
vector. Then identify the overlapping sequences between the
two sets of screened sequences. The silencer sequences that
are found in both sets (i.e., the overlapping part) are
removed from the sequences screened by the MAI-seq-
experiment vector. Ultimately, the remaining sequences are
identified as insulator sequences.

In summary, the insulators ultimately identified by the
MAI-seq system are: the sequences screened and identified
by the MAI-seq-experiment vector (insulators+silencers)
minus the overlapping sequences screened and identified by
both the MAI-seq-experiment and MAI-seq-control vectors
(silencers).

Furthermore, in the genome-wide insulator screening
system MAI-seq, the enhancer can be not only the SV40
Enhancer but also other enhancers such as the CMV
Enhancer, etc. The marker target gene can be not only the
GFP gene but also other genes such as RFP, mCherry, BFP,
etc.

Embodiment 2: Functional Validation of the
MAI-Seq-Experiment Vector in the Genome-Wide
Insulator Screening System MAI-Seq To validate whether MAI-seq can screen and identify
insulator sequences, the sequences of previously reported
insulators (Table 1) were cloned into the MAI-seq-experi-
ment vector. These included a control group (No Insulator)
and experimental groups with the sequences HS5_CBS,
Pax3_CBS1, Pax3_CBS2, Pax3_CBS3, SOX9_CBS1, and
SOX9_CBS2 from Table 1. The control and experimental groups were transfected into cells, and after 48 hours, the cells were collected and RNA was extracted. qPCR was used to detect changes in GFP gene expression (detection primers are shown in Table 2).

Figure 5:
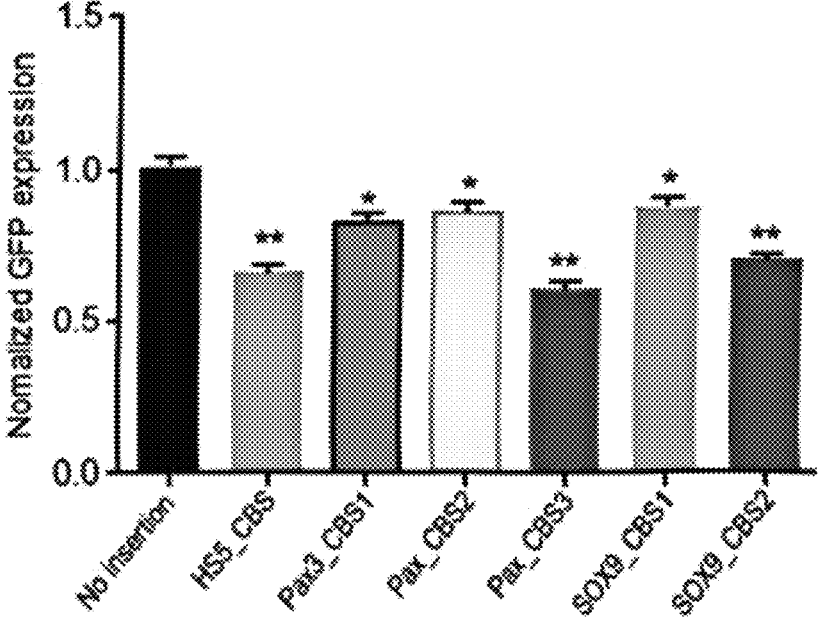
FIG. 5 shows the results of validating the insulation sequence screened by the MAI-seq-experiment vector: ** indicates a highly significant difference compared to the control group, $p<0.01$; * indicates a significant difference compared to the control group, $p<0.05$.

The results are shown in FIG. 5: compared to the control group, GFP expression in the experimental groups was significantly or extremely significantly reduced (in FIG. 5, ** indicates a highly significant difference compared to the control group, $p<0.01$; * indicates a significant difference compared to the control group, $p<0.05$). These results demonstrate that the reported insulator sequences in Table 1 can be efficiently detected using the MAI-seq-experiment vector, indicating that the MAI-seq-experiment vector can be used for the screening or identification of insulators.

TABLE 1

Information on Reported Insulators Used to Validate the MAI-seq-experiment Vector

| Sequence | Chromatin | Start Position | End Position | Reference Genome |
|---|---|---|---|---|
| HS5_CBS | Chr11 | 5310702 | 5313343 | hg19 |
| Pax3_CBS1 | Chr1 | 77942190 | 77944770 | mm10 |
| Pax3_CBS2 | chr1 | 77970975 | 77974415 | mm10 |
| Pax3_CBS3 | Chr1 | 77976869 | 77980896 | mm10 |
| SOX9_CBS1 | chr11 | 111536561 | 111538959 | mm10 |
| SOX9_CBS2 | Chr11 | 111533965 | 111536560 | mm10 |

TABLE 2 qPCR Detection Primer Sequences

| Primer Name | Sequence |
|---|---|
| GFP-F primer | 5'-ACCCTGAAGTTCATCTGCAC-3' (SEQ ID NO: 3) |
| GFP-R primer | 5'-CATGCCGTTTCATATGATCC-3' (SEQ ID NO: 4) |

Embodiment 3: Genome-Wide Insulator Screening Method 3.1 Preparation of Input Library Cultivate the target cells in which insulators need to be screened. When the cell confluence reaches 80%-90%, collect the cells and extract genomic DNA. Fragment the DNA into approximately 700 bp segments using an ultrasonic device, and then perform end-repair on the DNA fragments. Use the NEB® (NEB®; cat. no. E6000L) DNA Library Prep Kit to ligate Illumina® sequencing adapters (Illumina Inc®; cat. no. PE-400-1001) to 5 μg of the DNA fragments. Amplify the DNA using KAPA® amplification enzyme (KAPA Biosystems®; cat. no. KK2602) and primers containing vector homology arms. The primer sequences are as follows:

fw (SEQ ID NO:5): TAGAGCATGCACCGGACACTCTTTCCCTA-CACGACGCTCTTCCGAT CT;

rev (SEQ ID NO:6): GGCCGAATTCGTCGAGTGACTGGAGTTCA-GACGTGTGCTCTTCCG ATCT.

The fw (SEQ ID NO:5) and rev (SEQ ID NO:6) primers contain homology arm sequences that can undergo homologous recombination with both the MAI-seq-experiment vector and the MAI-seq-control vector. The DNA fragments amplified using these primers will also have homology arm sequences at both ends that can recombine with the MAI-seq-experiment and MAI-seq-control vectors. Through homologous recombination, the DNA fragments to be screened/tested can be inserted into the designated position of the vector (i.e., the insertion site for the sequence to be screened, as shown in FIG. 3 or 4 under "Insulator").

Next, PCR amplification is performed according to the set program (98° C. for 45 s; 98° C. for 15 s, 65° C. for 30 s, 72° C. for 30 s for 10 cycles). The amplification products are purified using magnetic beads (ratio of beads/PCR 0.8; cat. no. A63881) to obtain the constructed DNA fragments. The MAI-seq-experiment and MAI-seq-control vectors are linearized using the restriction enzymes SalI-HF and AgeI-HF. The enzyme-digested products are subjected to agarose gel electrophoresis, and the desired products are recovered to obtain the linearized vectors. Following the instructions of the homologous recombination kit (Nanjing Vazyme®, C117), the constructed DNA fragments are subjected to homologous recombination with the linearized MAI-seq-experiment and MAI-seq-control vectors, respectively, to construct homologous recombination plasmids. The homologous recombination plasmids are transformed into electrocompetent cells, and all transformation products are combined and placed in LB medium. The culture is shaken on a shaker at 37° C. and 200 rpm until the OD value of the bacterial suspension reaches 0.8-1.2. The plasmids are extracted using a kit (OMEGA®, D6902), and all plasmids are combined to form the Input library, which is then subjected to high-throughput sequencing.

3.2 Construction of Output Library

The constructed MAI-seq-experiment and MAI-seq-control input libraries are separately transfected into the target cells. After 24 hours of transfection, the transfected cells are collected separately. Total RNA is extracted from the collected cells using the M5 Universal Plus RNA Mini Kit, and mRNA with a poly (A) tail is enriched using the Dynabeads Oligo (dT) kit (Thermo Fisher Scientific®, 61005), which contains Oligo dT-coated magnetic beads.

Subsequently, the enriched mRNA is treated with TURBO™ DNase (Thermo Fisher Scientific®) to remove genomic DNA, and then purified using Agencourt RNA Clean XP beads (Beckman Coulter®). The mRNA is specifically reverse transcribed into target-specific first-strand complementary DNA (cDNA) using SuperScript III reverse transcriptase (Thermo Fisher Scientific®, 1.5 μg mRNA per reaction). The reverse transcription primer used is 5'-CAAACTCATCAATGTATCTTATCATG-3' (SEQ ID NO:7).

The cDNA is treated with RNase A+H and then purified using a PCR & DNA Clean up Kit. Finally, using this cDNA as a template, PCR amplification is performed with the following primers:

The forward primer F is 5'-AATGATACGGCGAC-CACCGAGATCTACACTCTTTCCCTA-CACGACGCTCTT CCGATCT-3' (SEQ ID NO:8);

The reverse primer R is 5'-CAAGCAGAAGACGGCAT-ACGAGAT-index-GTGACTGGAGTTCAGACGTG-3' (SEQ ID NO:9).

Each 50 μL PCR reaction mixture contains 5 μL of cDNA, and PCR amplification is performed using KAPA® amplification enzyme (KAPA Biosystems®; cat. no. KK2602) with the following program: 98° C. for 30 s for initial denaturation; 98° C. for 10 s for denaturation, 65° C. for 30 s for annealing, and 72° C. for 30 s for extension, for a total of 20 cycles. The amplified PCR products are subjected to agarose gel electrophoresis, and the target bands are recovered using a gel recovery kit to prepare the output libraries for the MAI-seq-experiment and MAI-seq-control vectors, respectively, which are then subjected to high-throughput sequencing.

The MAI-seq system (comprising MAI-seq-experiment and MAI-seq-control vectors) is used for homologous recombination with the sequence to be screened to obtain both the Input and Output libraries. These two libraries consist of two parts of data with different read types. The Input library is constructed by directly amplifying the insert fragments from the plasmid DNA used for cell transfection, serving as a reference for the original representation of insert fragments in the starting plasmid mixture. The Output library, on the other hand, is generated by measuring the abundance of mRNA transcribed from the insert fragments in the transfected plasmid pool.

3.3 Identification of Insulators

After obtaining the input and output sequencing data for the MAI-seq-experiment and MAI-seq-control vectors, the CRADLE software is used to process the data. To enhance the reliability of the final identified insulators, the following specific steps are taken:

First, only sequences with more than 20 reads in both the input and output libraries are selected for analysis.

Second, the BAM files for the input and output of both vectors are converted to BW files.

Third, the correctBias function is used to correct for technical biases in the read counts (shearing, PCR, mappability, G-quadruplex).

Fourth, the call peaks command is used to identify sequences with repressive effects. The key parameters are as follows: -rbin 300, -wbin 100, -d 20, -fdr 0.05.

Through these steps, sequences with reduced transcriptional abundance in the output library compared to the input library are selected. Then, the sequencing data from the input and output libraries of the MAI-seq-control vector are compared, and sequences with reduced transcriptional abundance in the output library compared to the input library are also selected. Subsequently, the sequences identified from both the MAI-seq-experiment and MAI-seq-control vectors are compared for overlapping parts. The sequences from the MAI-seq-experiment vector are used to remove the overlapping sequences, and the remaining sequences are identified as insulator sequences.

In summary, the final insulator sequences are those identified from the MAI-seq-experiment vector, with the overlapping sequences removed that were also identified from both the MAI-seq-experiment and MAI-seq-control vectors. The remaining sequences are the insulator sequences.

3.4 Validation of the MAI-Seq System

To validate the function of the MAI-seq system in screening for insulators, 30 sequences were synthesized, including 5 known insulator sequences, 5 known silencer sequences, and 20 negative sequences. Following the procedures outlined in sections 3.1 and 3.2 of Embodiment 3, the input and output libraries for the MAI-seq-experiment and MAI-seq-control vectors were constructed, and sequence identification was performed. The results showed that the MAI-seq-experiment vector system identified 10 sequences, including 5 silencers and 5 insulators, while the MAI-seq-control identified 5 silencer sequences. The overlapping sequences identified by both vectors were 5 silencer sequences, so the final sequences were 5 (5=10−5) insulator sequences, which was consistent with expectations. The validation results are shown in Table 3, demonstrating the efficiency and reliability of the MAI-seq system.

TABLE 3

Validation Results of the MAI-seq System

| Total Tested Sequence Types | Insulators | Silencers | Negative Sequences |
|---|---|---|---|
| Total Tested Sequence Count | 5 | 5 | 20 |
| Number of Sequences Screened by MAI-seq-experiment Vector | 5 | 5 | 0 |
| Number of Sequences Screened by MAI-seq-control Vector | 0 | 5 | 0 |
| Final Number of Insulators | 5 | 0 | 0 |

What is claimed is:

1. A genome-wide insulator screening system (MAI-seq), wherein the system comprises an MAI-seq-experiment vector and an MAI-seq-control vector; core gene elements in the MAI-seq-experiment vector are arranged in the following order: a weak promoter, a marker target gene, an insertion site for a sequence to be screened, an enhancer and a poly A site; core gene elements in the MAI-seq-control vector are arranged in the following order: a weak promoter, a marker target gene, an enhancer, an insertion site for the sequence to be screened and a poly A site; the insertion site for the sequence to be screened contains homologous arm sequences that are configured to hybridize with complementary sequences attached to the DNA sequence to be screened to enable homologous recombination, and after two ends of a DNA sequence to be screened are added to the homologous arm sequences, homologous recombination occurs with either the MAI-seq-experiment vector or the MAI-seq-control vector; and a nucleotide sequence of the MAI-seq-experiment vector is as shown in SEQ ID NO: 1, and a nucleotide sequence of the MAI-seq-control vector is as shown in SEQ ID NO:2.

2. A method for screening for genomic insulators using the genome-wide insulator screening system according to claim 1, comprising following steps:

S1: fragmenting a gene sequence to be tested, ligating the fragmented gene segments with sequencing adapters, and performing PCR amplification using primers as shown in SEQ ID NO:5 and SEQ ID NO:6;

S2: homologously recombining PCR products from S1 into the MAI-seq-experiment vector and the MAI-seq-control vector according to claim 1 to construct homologous recombination plasmids;

S3: transforming the homologous recombination plasmids constructed in S2 and extracting the plasmids to obtain an Input library for the MAI-seq-experiment vector and an Input library for the MAI-seq-control vector, respectively, and performing high-throughput sequencing on the Input libraries;

S4: transfecting cells with the Input libraries of the MAI-seq-experiment vector and the MAI-seq-control vector constructed in S3, collecting the cells, performing reverse transcription amplification, collecting amplified products to prepare an Output library for the MAI-seq-experiment vector and an Output library for the MAI-seq-control vector, respectively, and performing high-throughput sequencing on the Output libraries;

S5: by comparing sequencing data of the Input and Output libraries of the MAI-seq-experiment vector, screening out sequences with reduced transcription abundance in the Output library compared to the Input library;

S6: by comparing sequencing data of the Input and Output libraries of the MAI-seq-control vector, screening out sequences with reduced transcription abundance in the Output library compared to the Input library; and S7: removing from the sequences screened out in S5 those that are duplicated in the sequences screened out in S6, and defining sequences obtained after the removing as the screened insulator sequences.

3. A method for validating genomic insulators using the genome-wide insulator screening system according to claim 1, comprising following steps:

S1: inserting the sequence to be validated into the MAI-seq-experiment vector to construct a validation plasmid;

S2: using the MAI-seq-experiment vector without any sequence inserted as a blank control plasmid; and S3: transfecting cells with the blank control plasmid and the validation plasmid separately, collecting cells 48 hours post-transfection to extract RNA, and utilizing qPCR to detect changes in expression level of the marker target gene; and identifying the sequence to be validated is an insulator if the expression level of the marker target gene in the validation plasmid group decreases.

4. An insulator validation vector comprising the nucleotide sequence set forth in SEQ ID NO:1.

* * * * *

SEQUENCE LISTING

```
Sequence total quantity: 9
SEQ ID NO: 1          moltype = DNA   length = 5248
FEATURE               Location/Qualifiers
source                1..5248
                      mol_type = other DNA
                      organism = synthetic construct
SEQUENCE: 1
ggcctaactg gccggtacct gagctcccta ggtagagggt atataatgga agctcgactt   60
ccaggggccc gaattaattc gctgtctgcg agggccagct gttggggtga gtactccctc   120
tcaaaagcgg gcatgacttc tgcgctaaga ttgtcagttt ccaaaaacga ggaggatttg   180
atattcacct ggcccgcggt gatgcctttg agggtggccg cgtccatctg gtcagaaaag   240
acaatctttt tgttgtcaag cttgaggtgt ggcaggcttg agatctggcc atacacttga   300
gtgacaatga catccacttt gcctttctct ccacaggtgt ccactcccag gtccaactgc   360
aggtcgcctg caggcttaag catggctagc aaaggagaag aactcttcac tggagttgtc   420
ccaattcttg ttgaattaga tggtgatgtt aacggccaca agttctctgt cagtggagag   480
ggtgaaggtg atgcaacata cggaaaactt accctgaagt tcatctgcac tactggcaaa   540
ctgcctgttc cctggccaac actagtcact actctgtgct atggtgttca atgctttca   600
agatacccgg atcatatgaa acggcatgac tttttcaaga gtgccatgcc cgaaggttat   660
gtacaggaaa ggaccatctt cttcaaagat gacggcaact acaagacacg tgctgaagtc   720
aagtttgaag gtgataccct tgttaataga atcgagttaa aaggtattga cttcaaggaa   780
gatggcaaca ttctgggaca caaattggaa tacaactata actcacacaa tgtatacatc   840
atggcagaca aacaaaagaa tggaatcaaa gcgaacttca agacccgcca caacattgaa   900
gatggaagcg ttcaactagc agaccattat caacaaaata ctccaattgg cgatggccct   960
gtcctttttac cagacaacca ttacctgtcc acacaatctg ccctttcgaa agatcccaac   1020
gaaaagagag accacatggt ccttcttgag tttgtaacag ctgctgggat tacacatggc   1080
atggatgaac tgtacaactg atctagagca tgcaccggtg atatcgcggc cgcattaggc   1140
accccaggct ttacacttta tgcttccggc tcgtataatg tgtggatttt gagttaggat   1200
ccgtcgagat tttcaggagc taaggaagct aaaatggaga aaaaaatcac tggatatacc   1260
```

-continued

```
accgttgata tatcccaatg gcatcgtaaa gaacattttg aggcatttca gtcagttgct  1320
caatgtacct ataaccagac cgttcagctg gatattacgg ccttttttaaa gaccgtaaag  1380
aaaaataagc acaagtttta tccggccttt attcacattc ttgcccgcct gatgaatgct  1440
catccggaat tccgtatggc aatgaaagac ggtgagctgg tgatatggga tagtgttcac  1500
ccttgttaca ccgtttttcca tgagcaaact gaaacgtttt catcgctctg gagtgaatac  1560
cacgacgatt tccggcagtt tctacacata tattcgcaag atgtggcgtg ttacggtgaa  1620
aacctggcct atttccctaa agggtttatt gagaatatgt ttttcgtctc agccaatccc  1680
tgggtgagtt tcaccagttt tgatttaaac gtggccaata tggacaactt cttcgccccc  1740
gttttcacca tgggcaaata ttatacgcaa ggcgacaagg tgctgatgcc gctggcgatt  1800
caggttcatc atgccgtttg tgatggcttc catgtcggca gaatgcttaa tgaattacaa  1860
cagtactgcg atgagtggca gggcggggcg taaacgcgtg gatccggctt actaaaagcc  1920
agataacagt atgcgtattt gcgcgctgat ttttgcggta taagaatata tactgatatg  1980
tatcccgaa gtatgtcaaa aagaggtatg ctatgaagca gcgtattaca gtgacagttg  2040
acagcgacag ctatcagttg ctcaaggcat atatgatgtc aatatctccg gtctggtaag  2100
cacaaccatg cagaatgaag cccgtcgtct gcgtgccgaa cgctggaaag cggaaaatca  2160
ggaagggatg gctgaggtcg cccggtttat tgaaatgaac ggctcttttg ctgacgagaa  2220
cagggggctgg tgaaatgcag tttaaggttt acacctataa aagagagagc cgttatcgtc  2280
tgtttgtgga tgtacagagt gatattattg acacgcccgg gcgacggatg gtgatccccc  2340
tggccagtgc acgtctgctg tcagataaag tctcccgtga actttacccg gtggtgcata  2400
tcgggggatga aagctggcgc atgatgacca ccgatatggc cagtgtgccg gtctccgtta  2460
tcgggggaaga agtggctgat ctcagccacc gcgaaaatga catcaaaaac gccattaacc  2520
tgatgttctg gggaatataa atgtcaggct cccttataca cagccagtct cagggatatc  2580
gtcgacgaat tcggccggcc gcttcgagca gacatgataa gatacattga tgagtttgga  2640
caaaccacaa ctagaatgca gtgaaaaaaa tgctttatttt gtgaaatttg tgatgctatt  2700
gctttatttg taaccattat aagctgcaat aaacaagtta caacaacaa ttgcattcat  2760
tttatgtttc aggttcaggg ggaggtgtgg gaggtttttt aaagcaagta aaacctctac  2820
aaatgtggta aaatcgataa ggatccgacc gatgcccttg agagccttca acccagtcag  2880
ctccttccgg tgggcgcggg gcatgactat cgtcgccgca cttatgactg tcttccgagg  2940
atatcagatc tgcgcagcac catggcctga ataacctct gaaagaggaa cttggttagg  3000
taccttctga ggcggaaaga accagctgtg gaatgtgtgt cagttagggt gtggaaagtc  3060
cccaggctcc ccagcaggca gaagtatgca aagcatgcat ctcaattagt cagcaaccag  3120
gtgtggaaag tccccaggct ccccagcagg cagaagtatg caaagcatgc atctcaatta  3180
gtcagcaacc atagtcccgc ccctaactcc gcccatcccg cccctaactc cgcccagttc  3240
cgcccattct ccgccccatg gctgactaat tttttttatt acatgtgagc aaaaggccag  3300
caaaaggcca ggaaccgtaa aaaggccgcg ttgctggcgt ttttccatag gctccgcccc  3360
cctgacgagc atcacaaaaa tcgacgctca agtcagaggt ggcgaaaccc gacaggacta  3420
taaagatacc aggcgtttcc ccctggaagc tccctcgtgc gctctcctgt tccgaccctg  3480
ccgcttaccg gatacctgtc cgcctttctc ccttcgggaa gcgtggcgct ttctcatagc  3540
tcacgctgta ggtatctcag ttcggtgtag tcgttcgct ccaagctggg ctgtgtgcac  3600
gaaccccccg ttcagcccga ccgctgcgcc ttatccggta actatcgtct tgagtccaac  3660
ccggtaagac acgacttatc gccactggca gcagccactg gtaacaggat tagcagagcg  3720
aggtatgtag gcggtgctac agagttcttg aagtggtggc ctaactacgg ctacactaga  3780
agaacagtat ttggtatctg cgctctgctg aagccagtta ccttcggaaa aagagttggt  3840
agctcttgat ccggcaaaca aaccaccgct ggtagcggtg gtttttttgt ttgcaagcag  3900
cagattacgc gcagaaaaaa aggatctcaa gaagatcctt tgatcttttc tacggggtct  3960
gacgctcagt ggaacgaaaa ctcacgttaa gggattttgg tcatgagatt atcaaaaagg  4020
atcttcacct agatccttttt aaattaaaaa tgaagtttta aatcaatcta aagtatatat  4080
gagtaaactt ggtctgacag cggccgcaaa tgctaaacca ctgcagtggt taccagtgct  4140
tgatcagtga ggcaccgatc tcagcgatct gcctatttcg ttcgtccata gtggcctgac  4200
tccccgtcgt gtagatcact acgattcgtg agggcttacc atcaggcccc agcgcagcaa  4260
tgatgccgcg agagccgcgt tcaccggccc ccgatttgtc agcaatgaac cagccagcag  4320
ggagggccga gcgaagaagt ggtcctgcta ctttgtccgc ctccatccag tctatgagct  4380
gctgtcgtga tgctagagta agaagttcgc cagtgagtag tttccgaaga gttgtggcca  4440
ttgctactgg catcgtggta tcacgctcgt cgttcggtat ggcttcgttc aactctggtt  4500
cccagcggtc aagccgggtc acatgatcac ccatatttatg aagaaatgca gtcagctcct  4560
tagggcctcc gatcgttgtc agaagtaagt tggccgcggt gttgtcgctc atggtaatgg  4620
cagcactaca caattctctt accgtcatgc catccgtaag atgcttttcc gtgaccggcg  4680
agtactcaac caagtcgttt tgtgagtagt gtatacggcg accaagctgc tcttgcccgg  4740
cgtctatacg ggacaacacc gcgccacata gcagtacttt gaaagtgctc atcatcggga  4800
atcgttcttc ggggcggaaa gactcaagga tcttgccgct attgagatcc agttcgatat  4860
agcccactct tgcacccagt tgatcttcag catctttttac tttcaccagc gtttcggggt  4920
gtgcaaaaac aggcaagcaa aatgccgcaa agaaggggaat gagtgcgaca cgaaaatgtt  4980
ggatgctcat actcgtcctt tttcaatatt attgaagcat ttatcagggt tactagtacg  5040
tctctcaagg ataagtaagt aatattaagg tacgggaggt attggacagg ccgcaataaa  5100
atatctttat tttcattaca tctgtgtgtt ggttttttgt gtgaatcgat agtactaaca  5160
tacgctctcc atcaaaacaa aacgaaacaa aacaaactag caaaataggc tgtccccagt  5220
gcaagtgcag gtgccagaac atttctct                                      5248
```

SEQ ID NO: 2          moltype = DNA   length = 5248
FEATURE               Location/Qualifiers
source                1..5248
                      mol_type = other DNA
                      organism = synthetic construct
SEQUENCE: 2

```
ggcctaactg gccggtacct gagctccta ggtagaggt atataatgga agctcgactt   60
ccaggggccc gaattaattc gctgtctgcg agggccagct gttggggtga gtactccctc  120
tcaaaagcgg gcatgacttc tgcgctaaga ttgtcagttt ccaaaaacga ggaggatttg  180
atattcacct ggcccgcggt gatgcctttg agggtggccg cgtccatctg gtcagaaaag  240
acaatctttt tgttgtcaag cttgaggtgt ggcaggcttg agatctggcc atacacttga  300
```

-continued

```
gtgacaatga catccacttt gcctttctct ccacaggtgt ccactcccag gtccaactgc   360
aggtcgcctg caggcttaag catggctagc aaaggagaag aactcttcac tggagttgtc   420
ccaattcttg ttgaattaga tggtgatgtt aacggccaca agttctctgt cagtggagag   480
ggtgaaggtg atgcaacata cggaaaactt accctgaagt tcatctgcac tactggcaaa   540
ctgcctgttc cctggccaac actagtcact actctgtgct atggtgttca atgcttttca   600
agatacccgg atcatatgaa acggcatgac tttttcaaga gtgccatgcc cgaaggttat   660
gtacaggaaa ggaccatctt cttcaaagat gacggcaact acaagacacc gaggatatca   720
gatctgcgca gcaccatggc ctgaaataac ctctgaaaga ggaacttggt taggtacctt   780
ctgaggcgga aagaaccagc tgtggaatgt gtgtcagtta gggtgtggaa agtccccagg   840
ctccccagca ggcagaagta tgcaaagcat gcatctcaat tagtcagcaa ccaggtgtgg   900
aaagtcccca ggctccccag caggcagaag tatgcaaagc atgcatctca attagtcagc   960
aaccatagtc ccgcccctaa ctccgcccat cccgcccta actccgccca gttccgccca  1020
ttctccgccc catggctgac taatttttttt tattgtgctg aagtcaagtt tgaaggtgat  1080
acccttgtta atagaatcga gttaaaaggt attgacttca aggaagatgg caacattcgt  1140
ggacacaaat tggaatacaa ctataactca cacaatgtat acatcatggc agacaaacaa  1200
aagaatggaa tcaaagcgaa cttcaagacc cgccacaaca ttgaagatgg aagcgttcaa  1260
ctagcagacc attatcaaca aaatactcca attggcgatg gccctgtcct tttaccagac  1320
aaccattacc tgtccacaca atctgccctt tcgaaagatc ccaacgaaaa gagagaccac  1380
atggtccttc ttgagtttgt aacagctgct gggattacac atggcatgga tgaactgtac  1440
aactgatcta gagcatgcac cggtgatatc gcggccgcat taggcacccc aggctttaca  1500
ctttatgctt ccggctcgta taatgtgtgg attttgagtt aggatccgtc gagattttca  1560
ggagctaagg aagctaaaat ggagaaaaaa atcactggat ataccaccgt tgatatatcc  1620
caatggcatc gtaaagaaca ttttgaggca tttcagtcag ttgctcaatg tacctataac  1680
cagaccgttc agctggatat tacggccttt ttaaagaccg taaagaaaaa taagcacaag  1740
ttttatccgg cctttattca cattcttgcc cgcctgatga atgctcatcc ggaattccgt  1800
atggcaatga aagacggtga gctggtgata tgggatagtg ttcacccttg ttacaccgtt  1860
ttccatgagc aaactgaaac gttttcatcg ctctggagtg aataccacga cgatttccgg  1920
cagtttctac acatatattc gcaagatgtg gcgtgttacg gtgaaaacct ggcctatttc  1980
cctaaagggt ttattgagaa tatgtttttc gtctcagcca atccctgggt gagtttcacc  2040
agttttgatt taaacgtggc caatatggac aacttcttcg cccccgtttt caccatgggc  2100
aaatattata cgcaaggcga caaggtgctg atgccgctgg cgattcaggt tcatcatgcc  2160
gtttgtgatg gcttccatgt cggcagaatg cttaatgaat tacaacagta ctgcgatgag  2220
tggcagggcg gggcgtaaac gcgtggatcc ggcttactaa aagccagata acagtatgcg  2280
tatttgcgcg ctgatttttg cggtataaga atatatctat atgtatac cgaagtatg  2340
tcaaaaagag gtatgctatg aagcagcgta ttacagtgac agttgacagc gacagctatc  2400
agttgctcaa ggcatatatg atgtcaatat ctccggtctg gtaagcacaa ccatgcagaa  2460
tgaagcccgt cgtctgcgtg ccgaacgctg gaaagcggaa aatcaggaag ggatggctga  2520
ggtcgcccgg tttattgaaa tgaacggctc ttttgctgac gagaacaggg gctggtgaaa  2580
tgcagtttaa ggtttacacc tataaaagag agagccgtta tcgtctgttt gtggatgtac  2640
agagtgatat tattgacacg cccgggcgac ggatggtgat ccccctggcc agtgcacgtc  2700
tgctgtcaga taaagtctcc cgtgaacttt acccggtggt gcatatcggg gatgaaagct  2760
ggcgcatgat gaccaccgat atggccagtg tgccggtctc cgttatcggg gaagaagtgg  2820
ctgatctcag ccaccgcgaa aatgacatca aaaacgccat taacctgatg ttctggggaa  2880
tataaatgtc aggctccctt atacacagcc agtctgcagg atatcgtcga cgaattcggc  2940
cggccgcttc gagcagacat gataagatac attgatgagt ttggacaaac cacaactaga  3000
atgcagtgaa aaaaatgctt tatttgtgaa atttgtgatg ctattgcttt atttgtaacc  3060
attataagct gcaataaaca agttaacaac aacaattgca ttcattttat gtttcaggtt  3120
cagggggagg tgtgggaggt ttttttaaagc aagtaaaacc tctacaaatg tggtaaaatc  3180
gataaggatc cgaccgatgc ccttgagagc cttcaaccca gtcagctcct ccggtgggc  3240
gcggggcatg actatcgtcg ccgcacttat gactgtcttc acatgtgagc aaaaggccag  3300
caaaaggcca ggaaccgtaa aaaggccgcg ttgctggcgt ttttccatag gctccgcccc  3360
cctgacgagc atcacaaaaa tcgacgctca agtcagaggt ggcgaaaccc gacaggacta  3420
taaagatacc aggcgtttcc ccctggaagc tccctcgtgc gctctcctgt tccgaccctg  3480
ccgcttaccg gatacctgtc cgcctttctc ccttcgggaa gcgtggcgct ttctcatagc  3540
tcacgctgta ggtatctcag ttcggtgtag gtcgttcgct ccaagctggg ctgtgtgcac  3600
gaaccccccg ttcagcccga ccgctgcgcc ttatccggta actatcgtct tgagtccaac  3660
ccggtaagac acgacttatc gccactggca gcagccactg gtaacaggat tagcagagcg  3720
aggtatgtag cggtgctac agagttcttg aagtggtggc ctaactacgg ctacactaga  3780
agaacagtat ttggtatctg cgctctgctg aagccagtta ccttcgggaa aagagttggt  3840
agctcttgat ccggcaaaca aaccaccgct ggtagcggtg gtttttttgt ttgcaagcag  3900
cagattacgc gcagaaaaaa aggatctcaa gaagatcctt tgatcttttc tacggggtct  3960
gacgctcagt ggaacgaaaa ctcacgttaa gggattttgg tcatgagatt atcaaaaagg  4020
atcttcacct agatcctttt aaattaaaaa tgaagtttta aatcaatcta aagtatatat  4080
gagtaaactt ggtctgacag cggccgcaaa tgctaaacca ctgcagtggt taccagtgct  4140
tgatcagtga ggcaccgatc tcagcgatct gcctatttcg ttcgtccata gtggcctgac  4200
tcccgtcgt gtagatcact acgattcgtg agggcttacc atcaggcccc agcgcagcaa  4260
tgatgccgcg agagccgcgt tcaccggccc ccgatttgtc agcaatgaac cagccagcag  4320
ggagggccga gcgaagaagt ggtcctgcta ctttgtccgc ctccatccag tctatgagct  4380
gctgtcgtga tgctagagta agaagttcgc cagtgagtag tttccgaaga gttgtggcca  4440
ttgctactgg catcgtggta tcacgctcgt cgttcggtat ggcttcgttc aactctggtt  4500
cccagcggtc aagccgggtc acatgatcac ccatattatg aagaaatgca gtcagctcct  4560
tagggcctcc gatcgttgtc agaagtaagt tggccgcggt gttgtcgctc atggtaatgg  4620
cagcactaca caattctctt accgtcatgc catccgtaag atgcttttcc gtgaccggcg  4680
agtactcaac caagtcgttt tgtgagtagt gtatacggcg accaagctgc tcttgcccgg  4740
cgtctatacg ggacaacacc gcgccacata gcagtacttt gaaagtgctc atcatcggga  4800
atcgttcttc ggggcggaaa gactcaagga tcttgccgct attgagatcc agttcgatat  4860
agcccactct tgcacccagt tgatcttcag catcttttac tttcaccagc gtttcggggg  4920
gtgcaaaaac aggcaagcaa aatgccgcaa agaagggaat gagtgcgaca cgaaaatgtt  4980
ggatgctcat actcgtcctt tttcaatatt attgaagcat ttatcagggt tactagtacg  5040
```

-continued

```
tctctcaagg ataagtaagt aatattaagg tacgggaggt attggacagg ccgcaataaa    5100
atatctttat tttcattaca tctgtgtgtt ggttttttgt gtgaatcgat agtactaaca    5160
tacgctctcc atcaaaacaa aacgaaacaa aacaaactag caaaataggc tgtccccagt    5220
gcaagtgcag gtgccagaac atttctct                                       5248

SEQ ID NO: 3                moltype = DNA   length = 20
FEATURE                     Location/Qualifiers
source                      1..20
                            mol_type = other DNA
                            organism = synthetic construct
SEQUENCE: 3
accctgaagt tcatctgcac                                                        20

SEQ ID NO: 4                moltype = DNA   length = 20
FEATURE                     Location/Qualifiers
source                      1..20
                            mol_type = other DNA
                            organism = synthetic construct
SEQUENCE: 4
catgccgttt catatgatcc                                                        20

SEQ ID NO: 5                moltype = DNA   length = 48
FEATURE                     Location/Qualifiers
source                      1..48
                            mol_type = other DNA
                            organism = synthetic construct
SEQUENCE: 5
tagagcatgc accggacact ctttccctac acgacgctct tccgatct                        48

SEQ ID NO: 6                moltype = DNA   length = 49
FEATURE                     Location/Qualifiers
source                      1..49
                            mol_type = other DNA
                            organism = synthetic construct
SEQUENCE: 6
ggccgaattc gtcgagtgac tggagttcag acgtgtgctc ttccgatct                       49

SEQ ID NO: 7                moltype = DNA   length = 26
FEATURE                     Location/Qualifiers
source                      1..26
                            mol_type = other DNA
                            organism = synthetic construct
SEQUENCE: 7
caaactcatc aatgtatctt atcatg                                                 26

SEQ ID NO: 8                moltype = DNA   length = 58
FEATURE                     Location/Qualifiers
source                      1..58
                            mol_type = other DNA
                            organism = synthetic construct
SEQUENCE: 8
aatgatacgg cgaccaccga gatctacact ctttccctac acgacgctct tccgatct     58

SEQ ID NO: 9                moltype = DNA   length = 44
FEATURE                     Location/Qualifiers
source                      1..44
                            mol_type = other DNA
                            organism = synthetic construct
SEQUENCE: 9
caagcagaag acggcatacg agatgtgact ggagttcaga cgtg                             44
```